United States Patent
Hemstreet et al.

[11] Patent Number: 5,380,289
[45] Date of Patent: Jan. 10, 1995

[54] FLUID COLLECTION DEVICE

[75] Inventors: George P. Hemstreet, Oklahoma City; Karl H. Bergey, Norman; Robert E. Hurst; Rebecca B. Bonner, both of Oklahoma City, all of Okla.

[73] Assignee: The Board of Regents of the University of Oklahoma, Norman, Okla.

[21] Appl. No.: 5,488

[22] Filed: Jan. 19, 1993

[51] Int. Cl.[6] ............................................. A61M 1/00
[52] U.S. Cl. ................................... 604/317; 128/760; 128/771; 422/56
[58] Field of Search ........................ 128/760–762, 128/771; 604/317, 318, 403, 404; 422/16, 56, 60, 102; 436/63, 164, 165, 166; 435/39

[56] References Cited

U.S. PATENT DOCUMENTS

| | | | |
|---|---|---|---|
| 3,958,561 | 5/1976 | Bucalo | 128/762 |
| 4,534,881 | 8/1985 | Sikes et al. | 422/16 |
| 4,587,213 | 5/1986 | Malecki | 435/39 |
| 4,879,098 | 11/1989 | Oberhardt et al. | 128/762 |
| 4,953,561 | 9/1990 | Guirguis | 128/604 |
| 4,961,432 | 10/1990 | Guirguis | 128/760 |
| 5,038,793 | 8/1991 | Guirguis | 128/760 |
| 5,077,012 | 12/1991 | Guirguis | 128/760 |
| 5,108,381 | 4/1992 | Kolozsi | 128/760 |
| 5,137,031 | 8/1992 | Guirguis | 128/771 |

Primary Examiner—Randall L. Green
Assistant Examiner—Rob Clarke
Attorney, Agent, or Firm—Dunlap Codding Lee

[57] ABSTRACT

A fluid collection device having a primary container and a secondary container and a two stage fixation system for facilitating and controlling the fixation of cells in a sample of a biological fluid such as urine. The primary container generally comprises a plastic cup having a filtering apparatus disposed within it for filtering cells from the fluid. The primary container may contain a first stage fixative. The device further comprises a cover comprising a pressurizing chamber for forcing fluid through the filter and fixative delivery chamber for dispensing a fixative into the primary container. The filtered fluid may be reserved within a secondary container attached to the primary container. The filter having the cells retained on its surface is removable from the primary container for the purpose of laboratory analyses of the cells.

14 Claims, 3 Drawing Sheets

FLUID COLLECTION DEVICE

BACKGROUND

The present invention relates generally to devices used to collect and filter biological fluid samples for the purpose of preparing the samples to be analyzed and more particularly, but not by way of limitation, to urine collection devices for filtering and fixating cells in the urine in preparation for further analysis.

Urine collection for disease diagnosis is becoming routine but there are no devices currently available which combine the steps of urine collection, fixation and filtering in a single easy-to-use apparatus. Significant advances are being made in the understanding of tumor pathology of urinary carcinogenesis. For example, cancer diagnostic methods relying on the application of biomarkers to cells are becoming increasingly sophisticated. The measurement of such biomarkers in urine cells requires a prescribed fixation process in order to preserve the reactivity of the markers being assessed.

Additionally, there is increasing evidence of the importance of monitoring the protein composition or cellular content in the urine of individuals with occupational nephrotoxic exposure and of organ transplant patients. Kidney tubular cells shed into the urine may be extremely useful for monitoring the subclinical effects of various nephrotoxic agents of renal disease including those in the environment as well as those iatrogenically induced in the hospital situation associated with antibiotic and nephrotoxic chemotherapy.

Organ transplantation rejection may be monitored by collecting urine and quantitating the various types of cells exfoliated into the urine by using antibodies against available proximal, distal and convoluted tubular kidney cells. Hospital inpatients receiving pancreatic implants with small bowel fistulas draining into the bladder may also benefit from monitoring the number of pancreatic cells shed into the urine.

There is also a need for the proper collection and preservation of sputum and colon washings. Colon cytology specimens can be used in conjunction with various types of biomarkers for colon cancer diagnosis.

As the clinical procedures described above become more common and used on a wider scale, improved methods and devices for collecting and properly preparing fluid samples for testing will become paramount.

SUMMARY

The present invention comprises a biological fluid collection device, and more particularly a urine collection device comprising a container having a reactant system for facilitating and controlling the reaction of cells in a sample and having a filtering apparatus disposed within it. The filter allows the passage of fluid, proteins, and crystals while collecting cells on the upper surface of the filter. The container contains at least one reactant composition for reacting with the cells of the fluid. The reactant may be a fixative composition for fixating and preserving cells.

The device comprises at least two chambers. One chamber is a pump for applying pressure to the fluid within the container to force the fluid through the filter. Another chamber contains a reservoir of a reactant, such as a fixative, which is deliverable into the fluid within the container. The release of the second stage reactant may be timed. The two-stage reactant procedure promotes a controlled reaction of cells for later laboratory analysis. The filtrate maybe reserved within a secondary container attached to the first container. The filter having the cells retained on its surface is generally removable from the container for the purpose of laboratory analyses of the cells.

Prior to testing the cells of the fluid, it is desirable to separate the cells from the liquid portion of the fluid, and from the proteins, and crystals contained in the fluid. It is the object of the present invention to provide a simple effective and easy-to-use system which provides these results.

DESCRIPTION

The present invention is an apparatus for containing, reacting with and filtering a biological fluid containing cells in preparation for further analysis of the fluid sample.

As used herein, the term biological fluid is defined as a fluid containing cells and compounds of biological origin, and may include urine, bladder washings, colon washings, sputum or fluids from the respiratory, alimentary, circulatory or other body systems.

The device has a reactant system for preparing for laboratory analyses cells within the fluid such as bladder, kidney, pancreatic, intestinal or other epithelial cells. As used herein, the term reactant means a chemical composition which can react in some way with the cells of a biological fluid, the constituents of a biological fluid, or both and can include cell fixatives as well as other substances which react with cells or subcomponents thereof.

Figure 1:
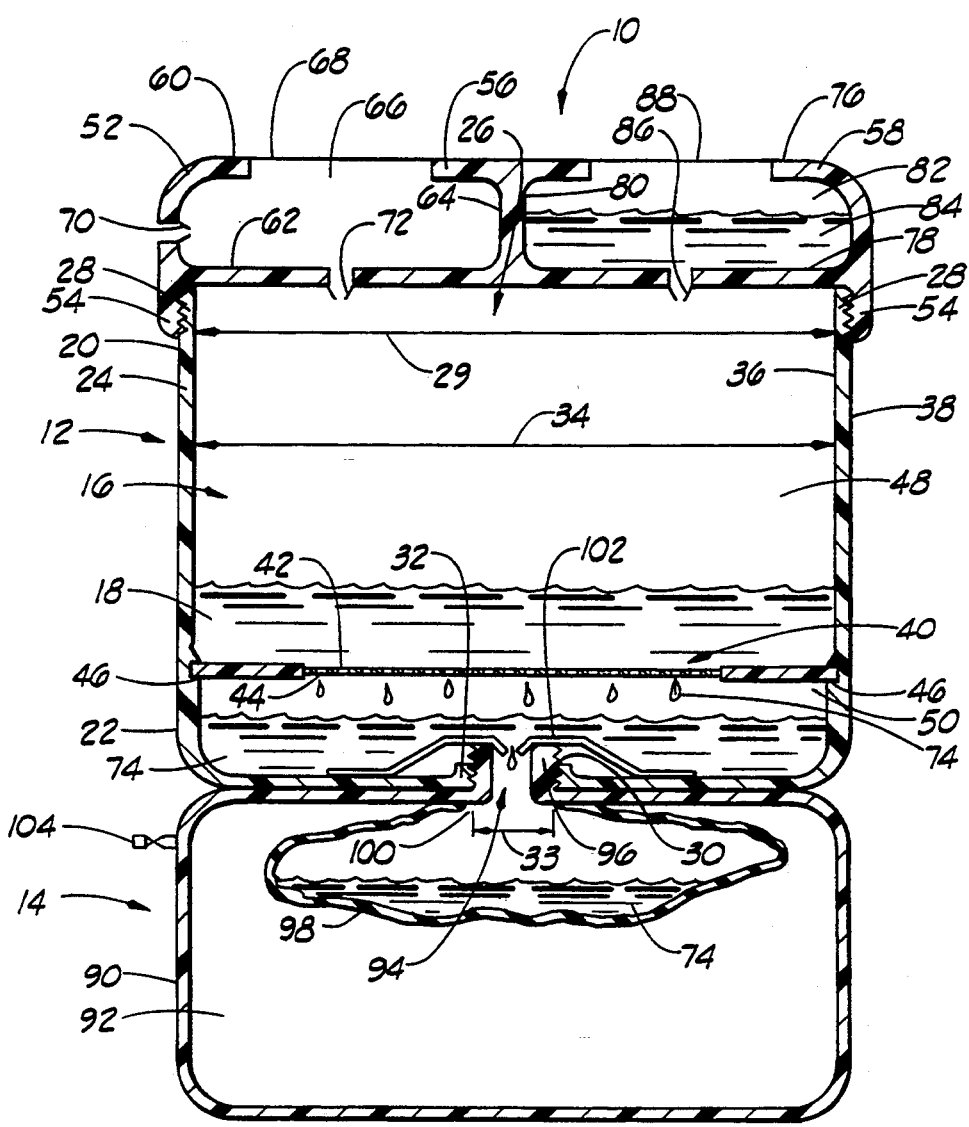
FIG. 1 shows a cross-sectional side view of one version of the invention.

A version of the device, referred to generally by the reference numeral 10 in FIG. 1, comprises a primary container 12 and a secondary container 14. Both the primary container 12 and the secondary container 14 are preferably made of a plastic. The primary container 12 has an interior space 16 for receiving a cell-containing biological fluid 18. The primary container 12 has an upper end 20, a lower end 22, a hollow body 24 extending from the lower end 22 to the upper end 20 and a first aperture 26 in the upper end 20 through which the biological fluid 18 is passed.

The primary container 12 further comprises a first engaging portion such as a threaded rim 28 on the upper end 20, a second aperture 30 in the lower end 22 and a second engaging portion such as a threaded rim 32 in the second aperture 30 on the lower end 22. The body 24 has an internal diameter 34 across the interior space 16. The threaded rim 28 has a width 29 substantially equal to the diameter 34 and the threaded rim 32 of the second aperture 30 has a width 33 substantially less than the diameter 34. The body 24 has an interior surface 36 and an exterior surface 38.

The device 12 further comprises a filtering device such as a filter assembly 40 for filtering the biological fluid 18. An example of a filter which may be used is a millipore filter. The filter 40 has an upper surface 42 and a lower surface 44. The filter 40 is disposed within the interior space 16 of the primary container 12. The primary container 12 has a filter support 46 for supporting and securely retaining the filter 40. The filter support 46 is mounted on the interior surface 36 of the body 24.

When the filter 40 is mounted on the filter support 46, the interior space 16 is subdivided by the filter 40 into an upper compartment 48 extending from the upper surface 42 of the filter 40 to the upper end 20 and a lower compartment 50 extending from the lower surface 44 of the filter 40 to the lower end 22. A first stage reactant, such as lypholyzed paraformaldehyde, a fixative (not shown), may be disposed within the upper compartment 48 prior to the passage of any fluid 18 into the upper compartment 48 for the purpose of causing a primary reaction of the fluid 18 or cells (not shown) in the fluid 18. As used herein, the term fixative is an agent employed in the preparation of a histologic or pathologic specimen, for the purpose of maintaining the existing form and structure of all its constituent elements.

The device 10 further comprises a lid 52 having an engaging portion such as a threaded rim 54 for threadly engaging the threaded rim 28 of the primary container 12 for covering the first aperture 26 of the primary container 12. In the preferred embodiment the lid 52 further comprises a pressurizing device or first chamber 56 and a reactant delivery portion or second chamber 58.

The first chamber 56 has an upper surface 60, a lower surface 62, and a side surface 64 extending between the upper surface 60 and the lower surface 62 to form an interior space 66. The first chamber 56 has a first pressure applying device, which in the preferred embodiment is a first push button 68, integrally incorporated into the upper surface 60 for applying pressure to the air within the first chamber 56 to form pressurized air.

The first chamber 56 also has a first one way valve 70 for allowing air into the interior space 66 and a second one way valve 72 for allowing the pressurized air from the interior space 66 of the first chamber 56 into the upper compartment 48 of the primary container 12. The second one way valve 72 functions to prevent the fluid 18 from backflowing from the upper compartment 48 into the interior space 66 of the first chamber 56 when the pressurized air from the first chamber 56 acts upon the fluid 18 thereby urging the fluid 18 through the filter 40 to form a filtrate 74 in the lower compartment 50. Primary container 12 may be modified to include a resin (not shown) or a column (not shown) for separating proteins from the filtrate 74.

The second chamber 58 of the lid 52 has an upper surface 76, a lower surface 78 and a side surface 80 extending between the upper surface 76 and the lower surface 78 to form an interior space 82 which serves as a reservoir for storing a second reactant 84, such as a second stage fixative. The second chamber 58 also comprises a third one way valve 86 for allowing passage of the reactant 84 into the upper compartment 48 of the primary container 12.

The second chamber 58 has a second pressure applying device, which in the preferred embodiment is a second push button 88, integrally incorporated into the upper surface 76 for applying pressure to the reactant 84 for delivering the reactant 84 through the third one way valve 86 into the upper compartment 48 of the primary container 12. After having been introduced into the upper compartment 48, the second stage reactant 84 mixes with the fluid 18 contained therein. The release of the reactant 84 from the second chamber 58 may be timed.

This version of device 10 further comprises the secondary container 14 for receiving filtrate 74 from the lower compartment 50 of the primary container 12. The secondary container 14 comprises a body 90 having an interior space 92 and a receiving aperture 94. The secondary container 14 has an engaging portion such as a threaded rim 96 for firmly and tightly threadly engaging the threaded rim 32 of second aperture 30 of the primary container 12.

Once the threaded rim 96 is engaged with the threaded rim 32, the second aperture 30 of the primary container 12 communicates with the receiving aperture 94 of the secondary container 14 thereby enabling the flow of filtrate 74 from the lower compartment 50 of the primary container 12 into the interior space 92 of the secondary container 14. In one version of the invention the secondary container 14 contains a flexible bag 98 having an opening 100 continuous with the receiving aperture 94 for receiving and storing filtrate 74 from the primary container 12.

The device 10 additionally comprises a check valve 102 which is operatively coupled with the second aperture 30 of the primary container 12 for regulating the direction of flow of filtrate 74 from the lower compartment 50 of the primary container 12 into the secondary container 14. The check valve 102 functions substantially prevent back flow of filtrate 74 from the secondary container 14 back through the second aperture 30 into the lower compartment 50 of the primary container 12. The secondary container 14 may have a relief valve 104 for reducing pressure build up in the secondary container 14.

Figure 2:
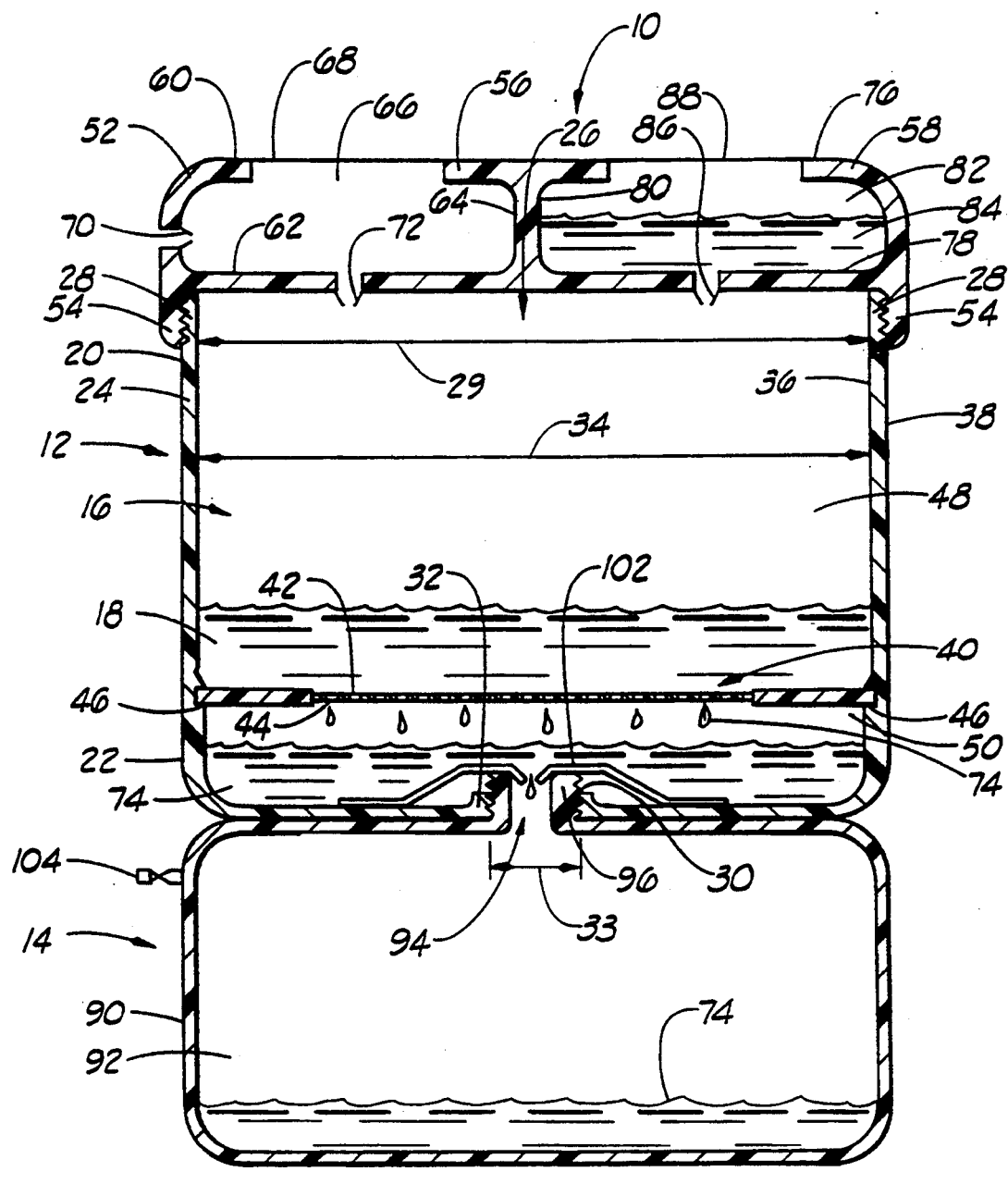
FIG. 2 shows a cross-sectional side view of another version of the invention.

In an alternative version of the device 10 shown in FIG. 2, in the secondary container 14 the flexible bag 98 may be absent, wherein the filtrate 74 is simply deposited into the interior space 92 of the secondary container 14.

Figure 3A:
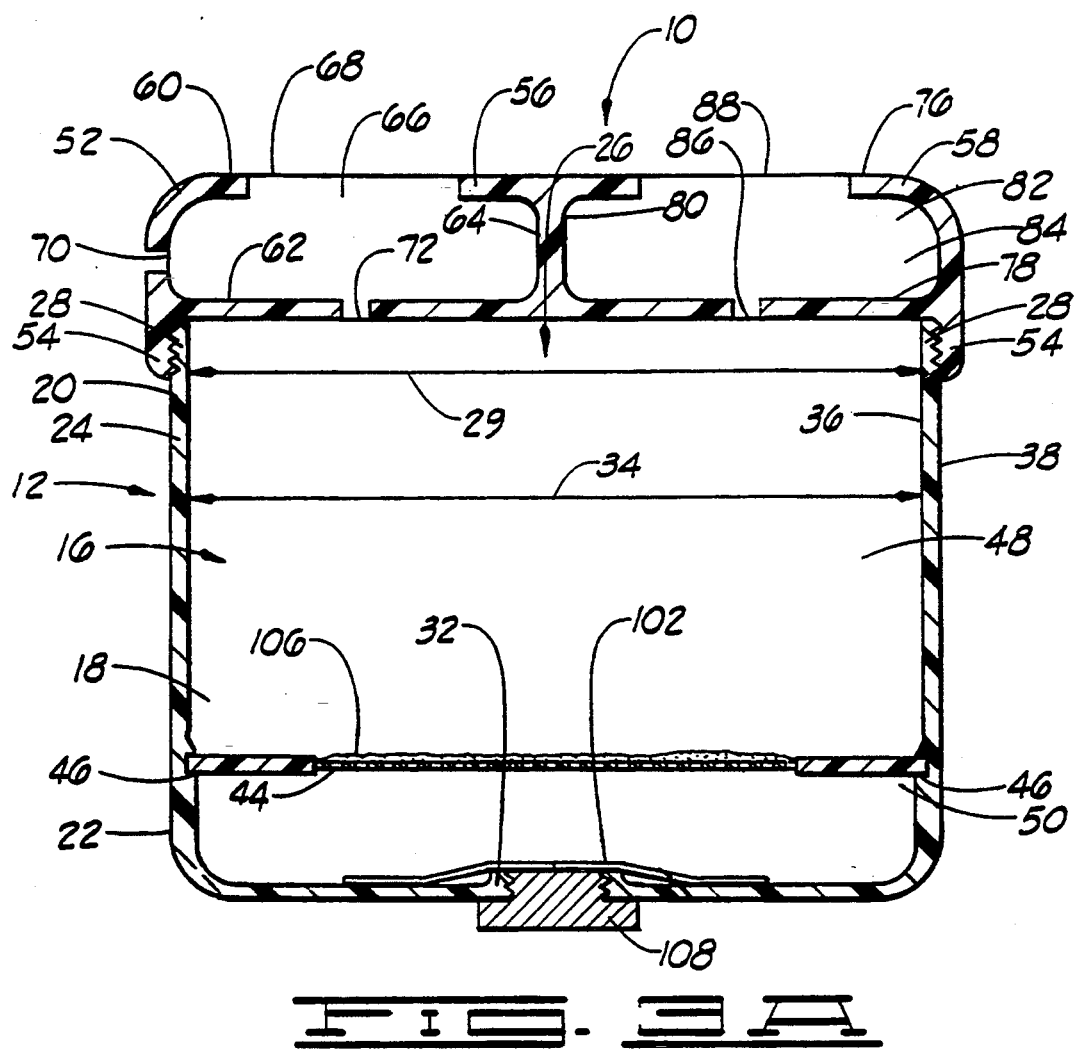
FIGS. 3A and 3B show the invention of FIG. 1 with the upper and lower container portions detached and stoppered.

After filtering, the filter 40 has accumulated cells 106 resting on the upper surface 42 (FIG. 3A).

Figure 3B:
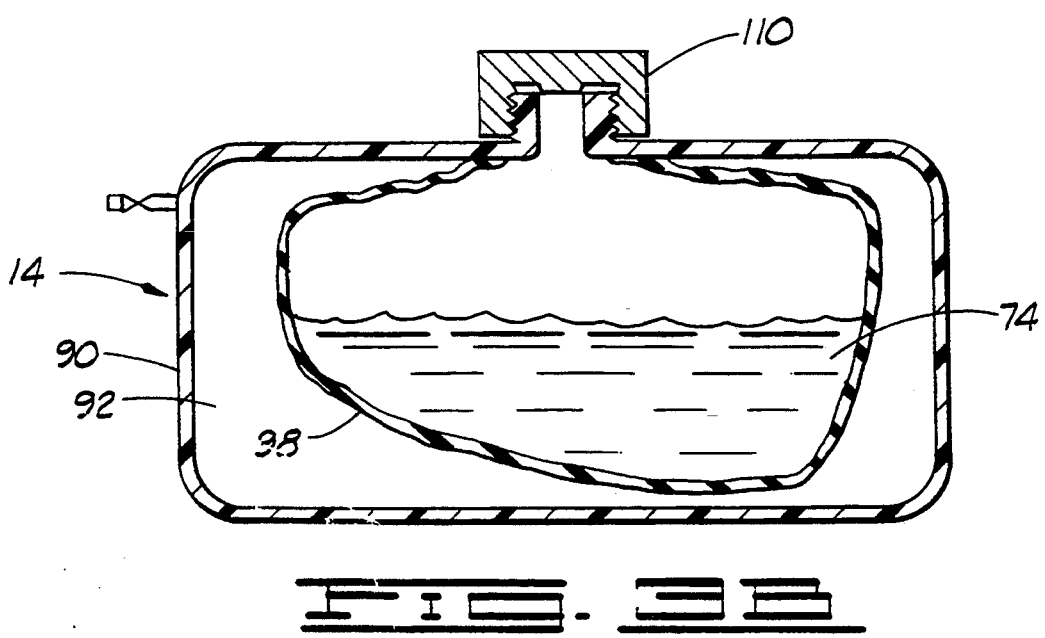

After completion of the filtering process, the primary container 12 may be separated from the secondary container 14 (FIGS. 3A and 3B). The second aperture 30 of the primary container 12 can be stoppered with a plug or cap 108 to inhibit leakage or contamination of the sample. The receiving aperture 94 of the secondary container 14 can similarly be stoppered with a plug or cap 110 to inhibit leakage of the filtrate 74 from the secondary container 14.

Figure 4:
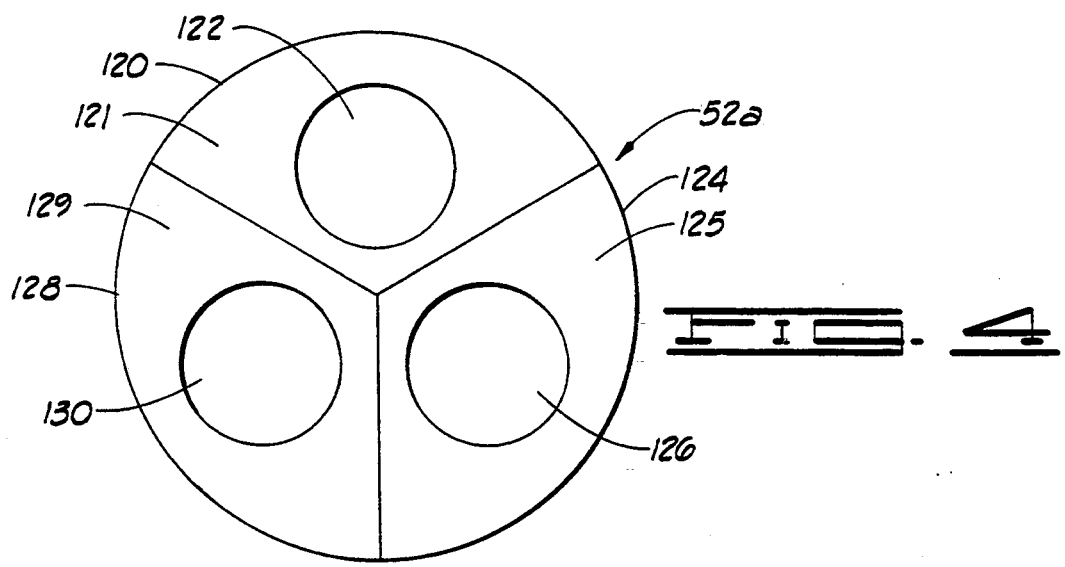
FIG. 4 shows a plan view of a lid having a pressurizing portion and two fixative delivery portions.

There may be more than one reactant delivery device in the apparatus. For example, in the version of the invention represented in FIG. 4, a lid 52 may comprise three compartments rather than two. A first compartment 120, similar to the first chamber 56, having an upper surface 121 and a push button 122 serves as the pressure applying device.

A second compartment 124, similar to the second chamber 58, having an upper surface 125 and a push button 126 serves as a fixative delivery system for delivering a fixative, stored in the second compartment 124, into the primary container 12.

A third compartment 128, similar to the second compartment 124, having an upper surface 129 and a push button 130 serves as another fixative delivery system for delivering another reactant or fixative, stored in the third compartment 128, into the primary container 12.

In Operation

The present invention provides a method for delivering a reactant such as a fixative to a biological fluid for preserving the cells in the fluid and for filtering the fluid for separating the cells from the fluid. In the method, a device, such as the device 10, having a container 12 and a filter assembly 40, and as described in detail previously and shown in FIG. 1, is provided. The container 12 contains a biological fluid sample 18, for example urine, in the first compartment 48. The fluid 18 has been previously deposited into the container 12 through the aperture 26 of the container 12. When fixation of the fluid 18 is desired, the first compartment 48 may have contained a reactant, such as the fixative paraformaldehyde, to provide initial fixation of the biological fluid 18 deposited into the first compartment 48. After the first reactant has reacted with the fluid, if so desired, a second reactant 84 can be delivered to the fluid 18 in the first compartment 48. This second reactant 84 is disposed in the second chamber 58 and is delivered to the fluid 18 in the first compartment 48 by applying pressure to the reactant 84 such that the reactant 84 is forced through a one-way valve 72 in the second chamber 58 and into the first compartment 48 where the reactant 84 can mix and react with the fluid 18. If the fluid 18 is urine and the reactant 84 is a fixative, the fixative causes the cells in the fluid 18 to cease living function and to remain in a preserved state until the sample is analyzed further.

In the version of the invention shown in FIGS. 1–4, pressure is applied to the reactant 84 by a pressure applying device 88 which is a push-button which functions by being pressed manually or automatically until an effective amount of the reactant 84 is delivered. The reactant 84 is allowed to react with the fluid 18 for a period of time adequate to provide the desired result such as cell fixation. If the container 12 is so equipped, a third reactant may be added to the fluid prior to filtration of the fluid 18.

The fluid 18 can then be urged through the filter assembly 40 for separating the cells from the fluid 18. The is done by applying pressure to the fluid 18 with a pressure applying device such as the push button 68. The cells are retained on the filter surface 42 and the fluid 18 which has passed through the filter assembly 40 into the second compartment 50 below the filter assembly 40 is the filtrate 74.

In the case that the fluid 18 is urine, the filtrate 74 is a urine filtrate and contains such elements as proteins, and crystals. The filtrate 74 may be removed from the container by passing it under pressure from the second compartment 50, through a check valve 102 and into a second container 14. The second container 14 may be detached from its connection with the first container 12 in preparation for shipping, storage, or other disposition.

Preferably, when the reactant delivered from the second chamber 58 is a fixative and the fluid 18 is urine, the fixative has a composition which preserves the cells with retention of characteristic morphology and quantity and distribution of biomarkers in the cells. More preferably, in such a case, the reactant 84 is a fixative composition which can inhibit the formation of crystals in the urine or solubilize crystals already present. This process of inhibition of crystal formation is important because crystals can (1) prevent or interfere with adherence of cells to a slide, (2) lengthen the time necessary to prepare the slide for analysis, and (3) physically obscure the viewing of cells on the slide. The benefits to the reduction of crystal formation in the sample are to (1) decrease preparation time, (2) decrease the number of unsatisfactory slides which are produced, and (3) increase the number of cells per microscope field on the slide.

The primary crystals inhibited by the method are common crystals comprising calcium and magnesium cations. Formation of certain rare crystalline forms may not be inhibited.

The term "inhibition of crystal formation" as used herein is defined as meaning the inhibition of the formation of crystals containing calcium or magnesium, or the solubilization of such crystals which are already present in urine samples which would otherwise form crystals under a range of temperatures including room temperature and refrigeration temperatures (e.g., about 4° C.) and during a range of time periods including immediately after collection of the sample, after 24 hours and after 48 hours or later if fixation was performed using a commonly used non-crystallization inhibiting composition such as buffered alcohol.

Inhibition of crystal formation allows the urine to be stored and shipped with its cells preserved. The fixative is designed to be mixed in equal volume with the urine. The fixative may consist of five components: A first component is a preservative which kills most bacteria and inhibits endogenous enzymatic degradation. A specific preservative is ethanol (50% v/v). A second component is a buffer to adjust the pH of the solution to help retain morphology, the buffer having a pK preferably in the range of 6–7 but alternatively in the ranges of 5–6 or 7–8. A preferred buffer is 2-N-morpholino-2-hydroxypropanesulfonic acid (MOPSO), 0.05M, which is also effective within the range of from about 0.01M to about 0.2M.

Other buffers in the preferred pK range are N-[2-Acetamido]-2-aminoethanesulfonic acid) (ACES), (N-[2-Acetamido]-2-iminodiacetic acid) (ADA), (bis[2-Hydroxyethyl]imino-tris[hydroxymethyl]methane (BIS-TRIS), (2-[N-Morpholino]ethanesulfonic acid (MES), and (Piperazine-N,N'-bis[2-ethanesulfonic acid] (PIPES). Buffers in the alternate pk range of 7–8 are (N,N-bis[2-Hydroxyethyl]-2-aminoethanesulfonic acid)(BES), (3-[N,N-bis(2-Hydroxyethyl)amino]-2-hydroxypropanesulfonic acid) (DIPSO), (N-[2-Hydroxyethyl]piperazine-N'-[3-propanesulfonic acid] (EPPS), (N-[2-Hydroxyethyl]piperazine-N'-[2-ethansulfonic acid] (HEPES), (N-[2-Hydroxyethyl]piperazine-N'-[2-hydroxypropanesulfonic acid]) (HEPPSO), (3-[N-Morpholino]propanesulfonic acid) (MOPS), (Piperazine-N,N'-bis[2-hydroxypropanesulfonic acid]) (POPSO), (3-[N-tris(Hydroxymethyl)methylamino]-2-hydroxypropanesulfonic acid) (TAPSO), and (N-tris[Hydroxymethyl]methyl-2-aminoethanesulfonic acid) (TES). These buffers are commercially available from a source such as Sigma Chemical Co.

A third component is a substance for inhibiting formation, and for solubilization, of crystals. Where the preservative is ethanol, the substance should be soluble in ethanol. A specific example is the dipotassium salt of ethylenediaminetetraacetic acid (EDTA). Other EDTA salts of cesium, rubidium, and various organic cations may also be effective, as are other salts, derivatives and analogs.

A fourth component is a substance to maintain the ionic strength within limits that inhibit cell distortion. A specific example is KCl, 0.10M, and it must be both soluble in the preservative (e.g., ethanol) and not cause precipitation of the solubilizing agent (e.g., potassium EDTA). Alternatively, the substance to maintain the ionic strength may be an additional amount of the buffer previously added or another compatible buffer.

A fifth component, which is optional, is a biocide to prevent the growth of certain resistant bacteria and other microorganisms. A specific example is $NaN_3$, sodium azide, 0.1% (w/v). This biocide component is optional depending on the time lapse between collection and shipment and analysis. The fixative is prepared by mixing the four aqueous components and adjusting the pH to 6.5, then adding an equal volume of pure ethanol.

Use of this, or similar, fixative compositions may be preceded by first mixing the urine sample with another fixative. An example, of such a fixative is a formaldehyde composition. The formaldehyde is added to the urine to reach a final concentration of 0.5% (w/v) and allowing the urine/formaldehyde mixture to stand for a time period, e.g., 15 minutes, prior to addition of the above fixative.

Changes may be made in the embodiments of the invention described herein or in parts of the elements of the embodiments described herein of in the steps or in the sequence of steps of the methods described herein without departing from the spirit and scope of the invention as defined in the following claims.

What is claimed is:

1. A method for delivering a reactant to and filtering cells in a biological fluid, the method comprising the steps of:
    providing a container, the container having a body extending from a first end to a second end and enclosing a space located therebetween,
        filtering means disposed within the space and mounted between the first end of the container and the second end of the container such that the space is subdivided into a first compartment between the filtering means and the first end and a second compartment between the filtering means and the second end, the filtering means comprising a filter having pores sized sufficiently small to inhibit passage of cells through the filter wherein when fluid is passed through the filter, cells are collected on the filter,
        a reactant dispenser for delivering reactant to a biological fluid upon actuation of the reactant dispenser, the reactant dispenser connected to the body and in communication with the space of the body, and
        a biological fluid disposed in the first compartment;
    actuating the reactant dispenser wherein a reactant held therein is automatically dispensed into the first compartment of the container for reacting with the cells of the biological fluid disposed in the container;
    passing the biological fluid through the filtering means wherein cells from the fluid are retained on the filtering means and a filtrate is formed as the fluid is passed through the filtering means into the second compartment; and
    removing the filtrate from the container.

2. The method of claim 1 wherein in the step of removing the filtrate from the container the filtrate is drained from the first-mentioned container into a second container which is connectable to and removable from the first container.

3. The method of claim 1 wherein in the step of providing a container, the biological fluid disposed therein is urine.

4. The method of claim 1 wherein in the step of actuating the reactant dispenser, the reactant is a cell fixative composition.

5. The method of claim 4 wherein the cell fixative composition has the property of inhibiting crystal formation in the biological fluid and of solubilizing crystals already in the biological fluid and wherein the characteristic morphology of the cells is retained.

6. A method for delivering a fixative to and filtering cells in a urine sample, the method comprising the steps of:
    providing a container, the container having
        a body extending from a first end to a second end and enclosing a space located therebetween,
        filtering means disposed within the space and mounted between tile first end of the container and the second end of the container such that the space is subdivided into a first compartment between the filtering means and the first end and a second compartment between the filtering means and the second end, the filtering means comprising a filter having pores sized sufficiently small to inhibit passage of cells through the filter wherein when urine is passed through the filter, cells in the urine are collected on the filter,
        a reactant dispenser for delivering a fixative to a biological fluid upon actuation of the reactant dispenser, the fixative dispenser connected to the body and in communication with the space of the body, and
        a urine sample disposed in the first compartment;
    actuating the fixative dispenser wherein a fixative held therein is automatically dispensed into the first compartment of the container for fixating the cells of the urine sample disposed in the container;
    passing the urine through the filtering means wherein cells from the urine are retained on the filtering means and a urine filtrate is formed as the fluid is passed through the filtering means into the second compartment; and
    removing the urine filtrate from the container.

7. The method of claim 6 wherein in the step of removing the urine filtrate from the container the urine filtrate is drained from the first-mentioned container into a second container which is connectable to and removable from the first container.

8. A method for delivering a fixative to and filtering cells in a urine sample, the method comprising the steps of:
    providing a container, the container having a body extending from a first end to a second end and enclosing a space located therebetween,
        filtering means disposed within the space and mounted between the first end of the container and the second end of the container such that the space is subdivided into a first compartment between the filtering means and the first end and a second compartment between the filtering means and the second end, the filtering means comprising a filter having pores sized sufficiently small to inhibit passage of cells through the filter wherein when urine is passed through the filter, cells in the urine are collected on the filter, a reactant dispenser for delivering a fixative to a biological fluid upon actuation of the reactant dispenser, the fixative dispenser connected to the body and in communication with the space of the body, and a urine sample disposed in the first compartment;

actuating the fixative dispenser wherein a fixative held therein is automatically dispensed into the first compartment of the container for fixating the cells of the urine sample disposed in the container and wherein the fixative has the property of inhibiting crystal formation in the urine and of solubilizing crystals already in the urine and wherein the characteristic morphology of the cells is retained;

passing the urine through the filtering means wherein cells from the urine are retained on the filtering means and a urine filtrate is formed as the fluid is passed through the filtering means into the second compartment; and removing the urine filtrate from the container.

9. A method for delivering a reactant to and filtering cells in a biological fluid, the method comprising the steps of:

providing a container, the container having a body extending from a first end to a second end and enclosing a space located therebetween, filtering means disposed within the space and mounted between the first end of the container and the second end of the container such that the space is subdivided into a first compartment between the filtering means and the first end and a second compartment between the filtering means and the second end, the filtering means comprising a filter having pores sized sufficiently small to inhibit passage of cells through the filter wherein when fluid is passed through the filter, cells are collected on the filter, a reactant dispenser for delivering a reactant to a biological fluid upon actuation of the reactant dispenser, the reactant dispenser connected to the body and in communication with the space of the body;

disposing a biological fluid into the first compartment;

actuating the reactant dispenser wherein a reactant held therein is automatically dispensed into the first compartment of the container for reacting with the cells of the biological fluid disposed in the container; and passing the biological fluid through the filtering means wherein cells from the fluid are retained on the filtering means and a filtrate is formed as the fluid is passed through the filtering means into the second compartment.

10. The method of claim 9 wherein the step of passing the biological fluid through the filtering means is followed by the step of removing the filtrate from the container.

11. A method for delivering a fixative to and filtering cells in a urine sample, the method comprising the steps of:

providing a container, the container having a body extending from a first end to a second end and enclosing a space located therebetween, filtering means disposed within the space and mounted between the first end of the container and the second end of the container such that the space is subdivided into a first compartment between the filtering means and the first end and a second compartment between the filtering means and the second end, the filtering means comprising a filter having pores sized sufficiently small to inhibit passage of cells through the filter wherein when urine is passed through :he filter, cells in the urine are collected on the filter, a reactant dispenser for delivering a fixative to a urine sample upon actuation of the reactant dispenser, the fixative dispenser connected to the body and in communication with the space of the body;

disposing a urine sample into the first compartment;

actuating the fixative dispenser wherein a fixative held therein is automatically dispensed into the first compartment of the container for fixating the cells of the urine sample disposed in the container; and passing the urine through the filtering means wherein cells from the urine are retained on the filtering means and a urine filtrate is formed as the fluid is passed through the filtering means into the second compartment.

12. The method of claim 11 wherein the step of passing the urine through the filtering means is followed by the step of removing the filtrate from the container.

13. A method for delivering a fixative to and filtering cells in a urine sample, the method comprising the steps of:

providing a container, the container having a body extending from a first end to a second end and enclosing a space located therebetween, filtering means disposed within the space and mounted between the first end of the container and the second end of the container such that the space is subdivided into a first compartment between the filtering means and the first end and a second compartment between the filtering means and the second end, the filtering means comprising a filter having pores sized sufficiently small to inhibit passage of cells through she filter wherein when urine is passed through the filter, cells in the urine are collected on the filter, a reactant dispenser for delivering a fixative to a biological fluid upon actuation of the reactant dispenser, the fixative dispenser connected to the body and in communication with the space of the body;

disposing a urine sample into the first compartment;

actuating the fixative dispenser wherein a fixative held therein is automatically dispensed into the first compartment of the container for fixating the cells of the urine sample disposed in the container and wherein the fixative has the property of inhibiting crystal formation in the urine and of solubilizing crystals already in the urine and wherein the characteristic morphology of the cells is retained; and passing the urine through the filtering means wherein cells from the urine are retained on the filtering means and a urine filtrate is formed as the fluid is passed through the filtering means into the second compartment.

14. The method of claim 13 wherein the step of passing the urine through the filtering means is followed by the step of removing the filtrate from the container.

* * * * *

UNITED STATES PATENT AND TRADEMARK OFFICE
CERTIFICATE OF CORRECTION

PATENT NO. : 5,380,289
DATED : January 10, 1995
INVENTOR(S) : Hemstreet et al.

It is certified that error appears in the above-identified patent and that said Letters Patent is hereby corrected as shown below:

Column 2, line 2, please delete "maybe" and substitute therefor -- may be --.

Column 2, line 11, after the word "simple" please insert -- , --.

Column 2, line 67, please delete "device 12" and substitute therefor -- device 10 --.

Column 4, line 12, before "second aperture 30" please insert -- the --.

Column 4, line 31, before the word "prevent" please insert -- to --.

Column 7, line 20, after the word "example" please delete ",".

Column 7, line 28, after the words "herein of" please delete "in".

Column 7, line 50, after the word "delivering" please insert -- a --.

Column 8, line 22, please delete "tile" and substitute therefor -- the --.

UNITED STATES PATENT AND TRADEMARK OFFICE
CERTIFICATE OF CORRECTION

PATENT NO. : 5,380,289
DATED : January 10, 1995
INVENTOR(S) : George P. Hemstreet, et al.

It is certified that error appears in the above-indentified patent and that said Letters Patent is hereby corrected as shown below:

Column 10, line 44, please delete "she" and substitute therefor -- the --.

Signed and Sealed this

Ninth Day of May, 1995

Attest:

BRUCE LEHMAN

*Attesting Officer*    *Commissioner of Patents and Trademarks*